United States Patent [19]

Harms et al.

[11] Patent Number: 5,092,867
[45] Date of Patent: Mar. 3, 1992

[54] CORRECTION AND SUPPORTING APPARATUS, IN PARTICULAR FOR THE SPINAL COLUMN

[76] Inventors: Jürgen Harms, Becchenweg 9, D-7517 Waldbronn-Reichenbach; Lutz Biedermann, Berta-Suttner-Str. 23, D-7730 Vs-Schwennningen, both of Fed. Rep. of Germany

[21] Appl. No.: 466,380
[22] PCT Filed: Jul. 11, 1989
[86] PCT No.: PCT/EP89/00802
§ 371 Date: Mar. 13, 1990
§ 102(e) Date: Mar. 13, 1990
[87] PCT Pub. No.: WO90/00377
PCT Pub. Date: Jan. 25, 1990

[30] Foreign Application Priority Data

Jul. 13, 1988 [DE] Fed. Rep. of Germany ....... 3823737

[51] Int. Cl.$^5$ .............................................. A61F 5/04
[52] U.S. Cl. .......................................... 606/61; 623/17
[58] Field of Search .................. 606/61, 60, 72, 73; 623/17

[56] References Cited

U.S. PATENT DOCUMENTS 3,865,105 2/1975 Lode ..................... 606/61
4,289,123 9/1981 Dunn ..................... 623/17 X
4,836,196 6/1989 Park et al. ............... 606/61
4,932,975 6/1990 Main et al. .............. 623/17

FOREIGN PATENT DOCUMENTS 0242708 10/1987 European Pat. Off. .
0340160 8/1989 European Pat. Off. .............. 606/61
3639810 5/1988 Fed. Rep. of Germany .
3711013 6/1988 Fed. Rep. of Germany .

Primary Examiner—Robert A. Hafer
Assistant Examiner—Kerry Owens
Attorney, Agent, or Firm—Donald Brown

[57] ABSTRACT

The invention relates to a correction and supporting apparatus. Such an apparatus is in particular used for stabilizing an injured spinal column. For allowing an easy adjustment of the vertebrae to be stabilized and a later readjustment four screws are provided each having a threaded shaft portion 7 and a receiver member 8 joined thereto. A first pair of threaded rods 45, 46 is provided for connecting a respective rod with two of the screws at the receiver member thereof forming a first connecting point, and a second pair of threaded rods 29, 30 is provided for connecting a respective one thereof with two of the screws at a second connecting point which is offset with respect to the first connecting point towards the threaded shaft portion.

5 Claims, 2 Drawing Sheets

CORRECTION AND SUPPORTING APPARATUS, IN PARTICULAR FOR THE SPINAL COLUMN

The invention refers to a correction and supporting apparatus as in particular used for the spinal column.

UNFALLCHIRURGIE, Vol. 12 (1986), pages 68-70 discloses the mechanical principle for the dorsal stabilisation of the pectoral and lumbar spinal column by means of a correction and supporting apparatus. The brochure "Fixateur Interne für die Wirbelsäule, Original-Instrumente und—Implantate der Schweizerischen Arbeitsgemeinschaft für Osteosynthesefragen-AO" discloses a fixateur interne or internal fixation device. This device comprises two pairs of so-called Schanz screws. A first pair thereof is screwed into the first vertebra through the arc roots (pediculus) on both sides and a second pair thereof is screwed into a second vertebra through the arc roots (pediculus) on both sides. The Schanz screws then have a shaft of a length of about 10 cm projecting from the vertebra. After mounting the four Schanz screws a partial reposition of the vertebra is already manually possible by means of the long projecting screw ends. Thereafter threaded rods are slipped onto respective two Schanz screws lying on the same side of the superposed vertebra. Thereupon the projecting free ends of the Schanz screws are again operated and the threaded rods are arrested. Finally those parts of the Schanz screws which project beyond the threaded rods are cut off. Thereafter the fixateur is covered with the muscles and the skin and the cut is closed. Whenever the surgeon will discover the next day that an adjustment of the angular position of the vertebra would be required, such an adjustment is no longer possible, because the projecting parts of the Schanz screws which are necessary for adjusting the angular position have already been removed. Moreover, the rotational flexibility of the apparatus is low.

The DE 36 39 810 A1 discloses an implant for correction and/or stabilization of the spinal column. The implant comprises screws having a threaded shaft part and a receiving part which is rigidly connected with the threaded shaft part and turned away therefrom. A respective pair of screws has the end thereof rigidly connected with a tie rod through the corresponding receiving part. Moreover, the pair of screws is additionally connected through a tension rod at a point in a distance from the connection between the receiving part and the tie rod. In order to allow an adjustment of the axial direction of the screws and the vertebra receiving the screws in a direction deviating from the parallel position, the connection between the tension rod and both screws is adjusted such that a flexion or bending strain is exerted onto the tie rod or the tension rod. This results in an uncontrollable material stress which may, in course of time, lead to a destruction of the tension rod and/or the tie rod. This may result in unpredictable problems in the interior of the body.

It is the object of the invention to provide a correction and supporting apparatus which allows the adjustment and the locking of the vertebra position in the sense of a longitudinal displacement and of an angular position (i.e. flexion of the spinal column forward or backward) without bending stress of the rods used therein. Such an adjustment and locking operation shall be facilitated as much as possible. A readjustment after the operation shall be possible. According to a further development a high stability with respect to the rotational movement exerted on the vertebrae and with respect to an axial load shall be obtained. Moreover, these aims shall be reached with an apparatus having a small front-to-back size.

These objects are achieved by means of a correction and supporting apparatus according to claim 1. Further embodiments of the invention are characterized in the dependent claims.

The screws to be used in the apparatus correspond to those described in the EP-0 242 708.

Further features and advantages of the invention will be apparent from a description of an embodiment in connection with the figures. In the figures.

Figure 1:
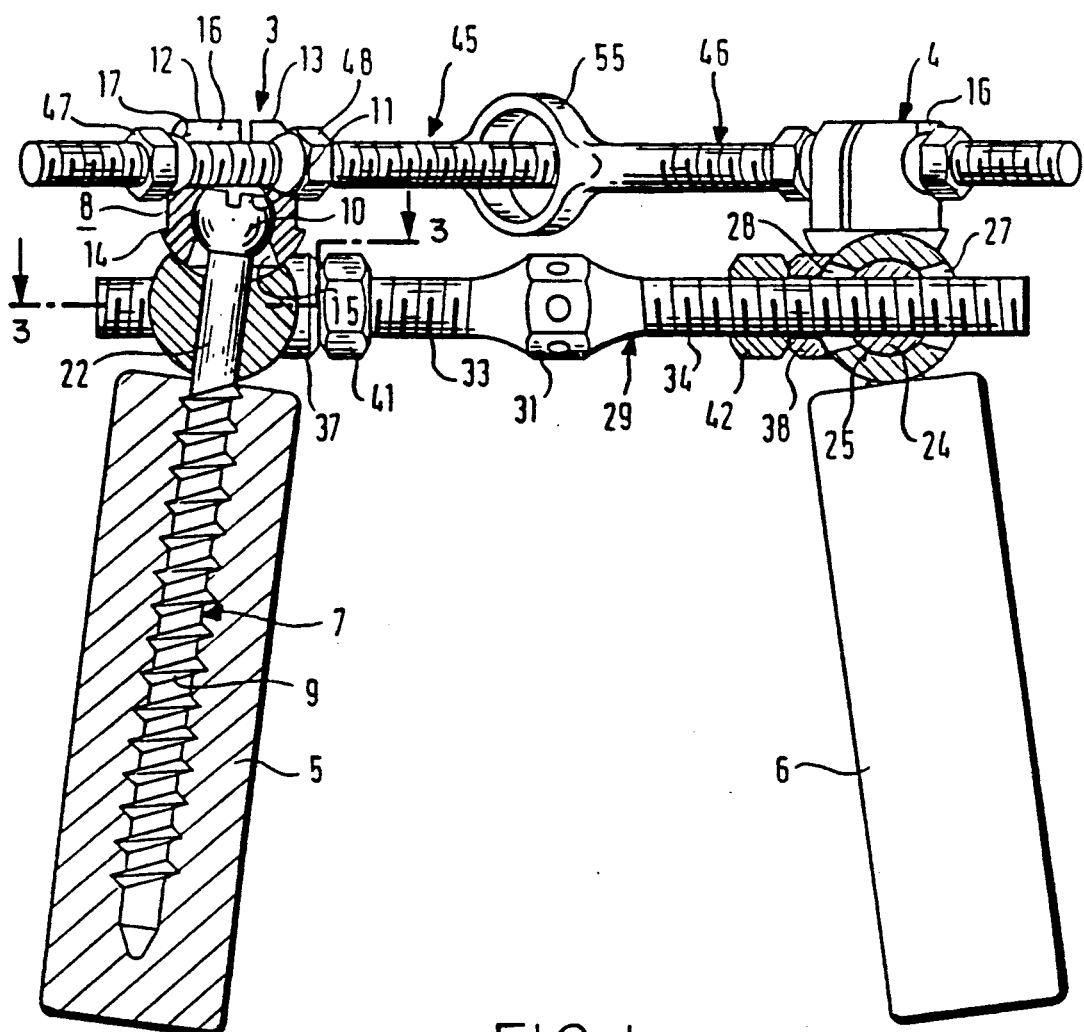
FIG. 1 shows a side view of the correction and supporting apparatus in partly sectional representation.
Figure 3:
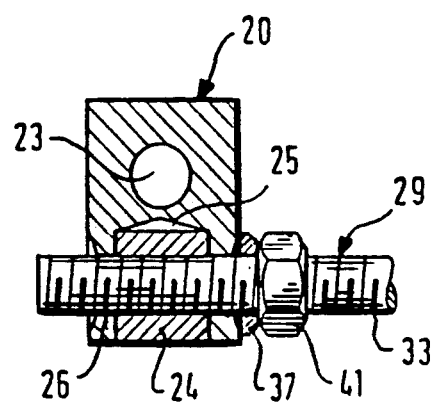
FIG. 3 is a section along line III—III in FIG. 1.

The correction and supporting apparatus comprises four screws 1-4 forming bone screws. In mounting the correction and supporting apparatus for stabilization of the spinal column the first pair of screws 1, S is screwed into the arc roots (pediculi) in a schematically indicated first vertebra 5. The second pair of screws 2, 4 is correspondingly screwed into the arc roots (pediculi) of an also schematically indicated second vertebra 6.

Each one of the respective screws 1-4 comprises a threaded shaft member 7 having a threaded portion 9 and a spherical segment shaped head 10 provided at the head end of the threaded shaft member, as well as a receiver member 8. The head has a plane surface 11 extending perpendicular to the axis of the threaded portion and being positioned at the side of the head facing away from the threaded portion 9. The plane surface further comprises at a position coaxial with the threaded portion a slot or a similar engagement providing member for a screw driver for screwing the screw into a vertebra.

The receiver member 8 comprises two head halves 12, 13 as well as a retaining ring 14 holding together the two head halves. Each head half comprises a hollow spherical segment shaped portion on the inner side thereof which faces the other head half, the inner radius of the hollow spherical segment shaped portion corresponding to the outer radius of the spherical segment shaped head 10. A neck portion 15 is adjacent to the spherical segment shaped portion. The neck portion is formed as a segment of a hollow spherical portion and is formed to be outwardly divergent from the spherical segment shaped portion. The axis of the neck portion passes through the center of the hollow spherical segment shaped portion. The spherical segment shaped portion has, on the side thereof opposite to the neck portion, a receiver groove 16 which extends perpendicular to the axis of symmetry of the neck portion and of the spherical segment shaped portion and which has a recess 17 formed in the outside thereof which is turned away to the other head half. The width of the receiver groove 16 is selected such that a threaded rod to be received may loosely be passed therethrough. In this manner the receiver member may freely pivot within a cone angle around the axis of the threaded shaft member 7 and may freely rotate around the axis of the screw for adjusting the direction of the groove.

Each screw comprises at a position between the receiver member 8 and the threaded portion 0 a cylindrical member 18-21 extending perpendicular to the screw axis. A bore 23 extends through the cylindrical member at one end thereof in a direction perpendicular to the cylinder axis. The diameter of the bore 23 is selected such that a neck 22 of the respective screw between the head and threaded portion thereof can properly be fitted into the bore. A bore 25 receiving a bolt 24 is provided at the other side of the cylindrical member coaxial with the axis thereof. The bolt 24 comprises a threaded bore formed perpendicular to the axis of the bore and to the cylinder axis. The dimensions of the bolt are selected such that it can be freely rotated around its own axis within the bore 25. A further bore 26 is provided in the cylinder in a direction perpendicular to the bore 23 and to the bore 25. This further bore 26 is coaxial with the threaded bore in the bolt such that a screw can be screwed therethrough into the bolt 24. Both ends of the bore 20 have conically widened portions 27, 28 in a direction parallel to the screw axis which allow a pivoting movement of the screws received therein around the longitudinal axis of the cylindrical member within a region defined by the conical widened portions.

Figure 2:
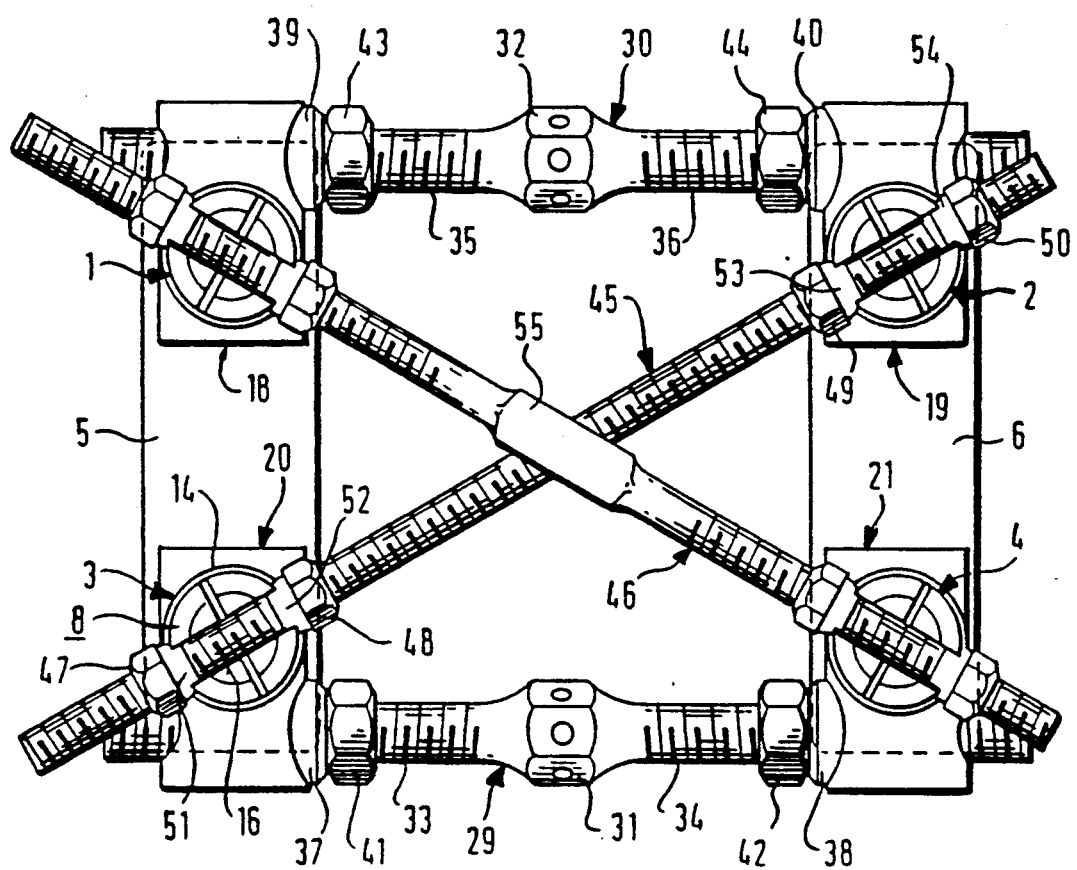
FIG. 2 shows a top view of the apparatus of FIG. 1.

The correction and supporting apparatus further comprises a pair of threaded rods 29, 30. These rods have a central portion thereof formed as a coaxial hexagon portion 31, 32 for engagement with a wrench and further threaded portions 33, 34; 35, 36 adjacent thereto on both sides. The respective opposite threaded portions 33, 34 and 35, 36 of a threaded rod are formed as oppositely directed right-handed threads and left-handed threads, resp. An intermediate member 37-40 acting as a washer is provided for each threaded portion. The intermediate member is formed with a plane surface on the side thereof facing the hexagon and with a hollow cylindrical segment shaped surface on the opposite side thereof. The curvatures of the latter surface corresponds to the curvatures of the outer surface of the respective cylindrical members 18-21. A respective nut 41-44 is provided between the hexagon portion and the intermediate member. As may be best seen from FIG. 2, a threaded rod 29 is connected with the two screws 3, 4 to be arranged on one side of the spinal column through the connecting cylindrical members 20, 21 by screwing the threaded portions into the bolts 24. The nuts 41-43 are not yet tightened, such that there is sufficient looseness and the screws may be screwed into the vertebrae. The threaded rod 30 is connected with the screws 1 and 2 through the associated cylindrical members in corresponding manner. After screwing the screws 1-4 into the associated parts of the vertebrae the nuts 37-40 are loosely tightened, such that a distance between the opposite screws 1, 2 and 3, 4, resp., is defined.

Further threaded rods 45 and 46 are provided. The threaded rod 45 is a simple threaded rod having two pairs of nuts 47, 48; 59, 50. The pairs of nuts have spherical segment shaped portions 51, 52 and 53, 54, resp., facing each other and being formed coaxial with the threaded rod. The respective head halves of the receiver member 8 comprise, as may be best seen from FIG. 1, spherical segment shaped recesses 17 formed coaxially with the corresponding receiver groove 16. The diameter of the threaded rod is selected such that it can just be inserted into the receiver grooves of the receiver members of the screws 1 and 4. The threaded rod 46 differs from the above described threaded rod 45 only in that it has a portion forming an eye 55 in the central region thereof. Otherwise the threaded rod is formed such that it can be inserted into the receiver groove of the screws 2 and 3. The eye 55 serves to pass the threaded rod 46 therethrough such that both screws or rods can be connected with the screws 1, 4 or 2, 3, resp., in virtually the same plane. Owing to the possibility of pivoting the receiver portions relative to the screws the insertion of the threaded rods 45, 46 is easily possible. After insertion the respective pairs of screws and rods are tightened for provisionally locking the threaded rods in relation to the receiver portions.

In operation it is started with drilling holes into the respective pairs of vertebra 5, 6 for receiving the screws 1-4. Thereafter a corresponding distance for the screws 1, 2 and 3, 4, resp , is adjusted by means of the threaded rods 29, 30 in dependence on the distance of the bores corresponding to the screws 1, 2 and 3, 4, resp. The screws 1-4 are then screwed into the prepared holes. Thereafter the threaded rods 45 and 46 are fitted into the associated grooves. The angular position of the vertebrae 5 and 6 in relation to each other is then adjusted by operating the nut pairs 47, 48 and 40, 50, resp. Simultaneously or in alternation therewith a change in distance may be obtained by adjusting the threaded rods 29 and 30. Following the desired adjustment the nuts 41-44 and the pairs of nuts 47, 48 and 49, 50 are tightened. The above described design enables the exact longitudinal and angular adjustment of the vertebrae and the repetition of such an adjustment at a later time with the same apparatus. Owing to the crossing threaded rods a high resistance to torsional forces is obtained. Since no parts of the apparatus are removed even after the adjustment operation, the apparatus remains fully operative for future readjustments.

I claim:

1. A correction and supporting apparatus for the spinal column, comprising pairs of screws, each having a threaded shaft portion and a receiver member connected thereto through a joint, a first pair of threaded rods for connection of a respective one of the rods with two of the screws at the receiver member thereof forming a first connecting point, and a second pair of threaded rods for connecting a respective one of the second pair of threaded rods with two of the screws at a second connecting point which is offset towards the threaded shaft portion with respect to the first connecting point, said threaded shaft portion and said receiver member of the screws are interconnected through a joint such that the receiver member is free to move in relation to the threaded shaft portion around a first axis and around a second axis which extends transversely to the first axis.

2. The correction and supporting apparatus according to claim 1 further including the rods of the second pair of threaded rods have their respective ends to be connected with the screws provided with opposite-handed threads.

3. The correction and supporting apparatus according to claim 1, further including the second pair of threaded rods is adapted to be connected with the screws to be screwed into a respective one of the sides of the spinal column.

4. The correction and supporting apparatus according to claim 3 further including one rod of the first pair comprises an eye for passing the second rod of the first pair therethrough.

5. The correction and supporting apparatus according to claim 1, further including each rod of the first pair of threaded rods is adapted for connection with the screw of the first pair provided for the first or second, resp., side on the one hand and with the screw of the second pair provided for the second or first, resp., side on the other hand.

* * * * *